(12) United States Patent
Karmon et al.

(10) Patent No.: US 7,576,177 B2
(45) Date of Patent: Aug. 18, 2009

(54) HSP PEPTIDES AND ANALOGS FOR MODULATION OF IMMUNE RESPONSES VIA ANTIGEN PRESENTING CELLS

(75) Inventors: Yoram Karmon, Petah Tikva (IL); Ann Avron, Rehovot (IL); Dana Elias, Gedera (IL)

(73) Assignee: Andromeda Biotech Ltd., Rehovot (IL)

( * ) Notice: Subject to any disclaimer, the term of this patent is extended or adjusted under 35 U.S.C. 154(b) by 572 days.

(21) Appl. No.: 10/902,923

(22) Filed: Jul. 30, 2004

(65) Prior Publication Data
US 2005/0163746 A1 Jul. 28, 2005

Related U.S. Application Data

(63) Continuation of application No. PCT/IL03/00078, filed on Jan. 30, 2003.

(60) Provisional application No. 60/352,594, filed on Jan. 31, 2002.

(51) Int. Cl.
*C07K 14/00* (2006.01)
(52) U.S. Cl. ...................................... 530/350
(58) Field of Classification Search ........................ None
See application file for complete search history.

(56) References Cited

U.S. PATENT DOCUMENTS

| | | | |
|---|---|---|---|
| 5,114,844 A | 5/1992 | Cohen et al. | 435/7.21 |
| 5,348,945 A | 9/1994 | Berberian et al. | 514/21 |
| 5,578,303 A | 11/1996 | Cohen et al. | 424/93.71 |
| 5,671,848 A | 9/1997 | Cohen et al. | 206/569 |
| 5,736,146 A | 4/1998 | Cohen et al. | 424/194.11 |
| 5,780,034 A | 7/1998 | Cohen et al. | 424/185.1 |
| 5,869,058 A | 2/1999 | Cohen et al. | 424/194.11 |
| 5,958,416 A | 9/1999 | Birnbaum et al. | 424/190.1 |
| 5,993,803 A | 11/1999 | Cohen et al. | 424/93.71 |
| 6,180,103 B1 | 1/2001 | Cohen et al. | 424/185.1 |
| 6,322,790 B1 | 11/2001 | Srivastava | 424/193.1 |

FOREIGN PATENT DOCUMENTS

| | | |
|---|---|---|
| EP | 0 262 710 B1 | 8/1992 |
| JP | 9-241159 | 9/1997 |
| JP | 10-212230 | 8/1998 |
| WO | WO 89/12455 | 12/1989 |
| WO | WO 91/02542 | 3/1991 |
| WO | WO 92/04049 | 3/1992 |
| WO | WO 94/02509 | 2/1994 |
| WO | WO 94/03208 * | 2/1994 |
| WO | WO 94/29459 | 12/1994 |
| WO | WO 95/25744 | 9/1995 |
| WO | WO 96/10039 | 4/1996 |
| WO | WO 96/16083 | 5/1996 |
| WO | WO 96/18646 | 6/1996 |
| WO | WO 96 19236 * | 6/1996 |
| WO | WO 96/19236 | 6/1996 |
| WO | WO 97/01959 | 1/1997 |
| WO | WO 97/11966 | 4/1997 |
| WO | WO 98/08536 | 3/1998 |
| WO | WO 00/27870 | 5/2000 |
| WO | WO 01/04344 A2 | 1/2001 |
| WO | WO 01/43691 A2 | 6/2001 |

OTHER PUBLICATIONS

Ngo et al., in The Protein Folding Problem and Tertiary Structure Prediction, 1994, Merz, et al., (ed.), Birkhauser, Boston, MA, pp. 433 and 492-495.*
Burgess et al., J of Cell Bio. 111:2129-2138, 1990.*
Lazar et al. Molecular and Cellular Biology 8:1247-1252, 1988.*
Bowie et al. Science, 247:1306-1310, 1990, p. 1306, col. 2.*
Aoki et al (Cancer Immunol Immunother. Nov 2001 ;50(9):463-8).*
Zitvogel et al (J Exp Med. Jan. 1, 1996;183(1):87-97).*
Springer (Nature Aug. 1990 346:425-435).*
Ohad S. Birk, et al., "The 60-kDa Heat Shock Protein Modulates Allograft Rejection", Proc. Natl. Acad. Sci. USA, vol. 96, pp. 5159-5163 (1999).
Tatsuya Ohkawara, et. al., "Amelioration of Dextran Sulfate Sodium-Induced Colitis by Anti-macrophage Migration Inhibitory Factor Antibody in Mice", Gastroenterology, vol. 12, pp. 256-270 (2002).
Omathanu Pillai, et al., "Polymers In Drug Delivery", Current Opinion in Chemical Biology, vol. 5, pp. 447-451 (2001).
Koji Ohashi, et al., "Cutting Edge: Heat Shock Protein 60 Is a Putative Endogenous Ligand of the Toll-Like Receptor-4 Complex", Journal of Immunology, The American Association of Immunologists, pp. 558-561 (2000).
Michael Mähler, et al., "Genetic Analysis of Susceptibility to Dextran Sulfate Sodium-Induced Colitis in Mice", Genomics, vol. 55, pp. 147-156 (1999).
Charles A. Janeway, Jr., "How The Immune System Works To Protect The Host From Infection: A Personal View", PNAS, vol. 98, No. 13, pp. 7461-7468 (2001).

(Continued)

*Primary Examiner*—Christopher H Yaen
(74) *Attorney, Agent, or Firm*—Winston & Strawn, LLP

(57) ABSTRACT

According to the present invention it is now disclosed that exposure of antigen presenting cells, particularly dendritic cells, to peptides or peptide analogs derived from heat shock proteins will subsequently activate T cells to produce immunomodulatory cytokines and will directly influence the cytokines, chemokines, and surface antigens produced by the exposed antigen presenting cells. The present invention relates to peptides and peptide analogs of heat shock proteins capable of interacting directly with dendritic cells. The present invention further relates to pharmaceutical compositions that include dendritic cells exposed to such peptides and analogs, useful for prevention or treatment of either inflammatory disorders and autoimmune diseases or malignancies, viral infections and allergy.

7 Claims, 5 Drawing Sheets

OTHER PUBLICATIONS

Michael Whelan, et al., "A Filarial Nematode-Secreted Product Signals Dendritic Cells to Acquire a Phenotype that Drives Development of Th2 Cells", Journal of Immunology, vol. 164, pp. 6453-6460 (2000).

Wei Chen, et al., "Human 60-kDa Heat-Shock Protein: A Danger Signal to the Innate Immune System", The American Association of Immunologists, Journal of Immunology, vol. 162, pp. 3212-3219 (1999).

Colin C. Anderson, et al., "Danger: The View From The Bottom Of The Cliff", Seminars in Immunology, vol. 12, pp. 231-238 (2000).

Dana Elias, et al., "Vaccination Against Autoimmune Mouse Diabetes With A T-Cell Epitope Of The Human 65-kDa Heat Shock Protein", Proc. Natl. Acad. Sci. USA, vol. 88, pp. 3088-3091, Medical Sciences (1991).

Willem van Eden, et al., "Cloning Of The Mycobacterial Epitope Recognized By T Lymphocytes In Adjuvant Arthritis", Nature, vol. 331, pp. 171-173 (1988).

Willem van Eden, et al., "Do Heat Shock Proteins Control The Balance Of T-Cell Regulation In Inflammatory Diseases?", Immunology Today, Copyright © 1998 Elsevier Science Ltd., (1998).

Jörg Becker, et al., "Review, Heat-Shock Proteins As Molecular Chaperones", Eur. J. Biochem., vol. 219, pp. 11-23 (1994).

Suzue et al., "Heat Shock Fusion Proteins As Vehicles For Antigen Delivery Into The Major Histocompatibility Complex Class 1 Presentation Pathway", Proc. Natl. Academy. Sci., vol. 94, No. 24, pp. 13146-13151 (1997).

P. Srivastava, "Interation Of Heat Shock Proteins With Peptides And Antigen Presenting Cells; Chaperoning Of The Innate And Adaptive Immune Responses", Annu. Rev. Immunol., vol. 20, pp. 395-425 (2002).

Srivastava et al., "Heat Shock Protein Transfer Peptides During Antigen Processing And CTL Printing", Immunogenetics, vol. 39, No. 2, pp. 93-98 (1994).

Harpreet Singh-Jasuja et al., "The Heat Shock Protein gp96 Induces Maturation Of Dendritic Cells And Down-Regulation Of Its Receptor", Eur. J. Immunol, vol. 30, pp. 2211-2215 (2000).

Robert J. Binder et al., "Cutting Edge: Heat Shock Protein gp96 Induces Maturation and Migration of CD11c$^+$ Cells In Vivo", Journal of Immunology, vol. 165, pp. 6029-6035 (2000).

Itamar Raz, et al., "β-Cell Function In New-Onset Type 1: Diabetes And Immunomodulation With A Heat-Shock Protein Peptide (Diapep277): A Randomised, DoubleBlind, Phase II Trial", The Lancet, vol. 358 No. 9295, pp. 1749-1753 (2001).

* cited by examiner

SEQUENCE LISTING

<160> NUMBER OF SEQ ID NOS: 9

<210> SEQ ID NO 1
<211> LENGTH: 573
<212> TYPE: PRT
<213> ORGANISM: Homo sapien

<400> SEQUENCE: 1

Met Leu Arg Leu Pro Thr Val Phe Arg Gln Met Arg Pro Val Ser Arg
1               5                   10                  15

Val Leu Ala Pro His Leu Thr Arg Ala Tyr Ala Lys Asp Val Lys Phe
            20                  25                  30

Gly Ala Asp Ala Arg Ala Leu Met Leu Gln Gly Val Asp Leu Leu Ala
        35                  40                  45

Asp Ala Val Ala Val Thr Met Gly Pro Lys Gly Arg Thr Val Ile Ile
    50                  55                  60

Glu Gln Gly Trp Gly Ser Pro Lys Val Thr Lys Asp Gly Val Thr Val
65                  70                  75                  80

Ala Lys Ser Ile Asp Leu Lys Asp Lys Tyr Lys Asn Ile Gly Ala Lys
                85                  90                  95

Leu Val Gln Asp Val Ala Asn Asn Thr Asn Glu Glu Ala Gly Asp Gly
            100                 105                 110

Thr Thr Thr Ala Thr Val Leu Ala Arg Ser Ile Ala Lys Glu Gly Phe
        115                 120                 125

Glu Lys Ile Ser Lys Gly Ala Asn Pro Val Glu Ile Arg Arg Gly Val
    130                 135                 140

Met Leu Ala Val Asp Ala Val Ile Ala Glu Leu Lys Lys Gln Ser Lys
145                 150                 155                 160

Pro Val Thr Thr Pro Glu Glu Ile Ala Gln Val Ala Thr Ile Ser Ala
                165                 170                 175

Asn Gly Asp Lys Glu Ile Gly Asn Ile Ile Ser Asp Ala Met Lys Lys
            180                 185                 190

Val Gly Arg Lys Gly Val Ile Thr Val Lys Asp Gly Lys Thr Leu Asn
        195                 200                 205

Asp Glu Leu Glu Ile Ile Glu Gly Met Lys Phe Asp Arg Gly Tyr Ile
    210                 215                 220

Ser Pro Tyr Phe Ile Asn Thr Ser Lys Gly Gln Lys Cys Glu Phe Gln
225                 230                 235                 240

```
Asp Ala Tyr Val Leu Leu Ser Glu Lys Lys Ile Ser Ile Gln Ser
            245                 250                 255

Ile Val Pro Ala Leu Glu Ile Ala Asn Ala His Arg Lys Pro Leu Val
            260                 265                 270

Ile Ile Ala Glu Asp Val Asp Gly Glu Ala Leu Ser Thr Leu Val Leu
            275                 280                 285

Asn Arg Leu Lys Val Gly Leu Gln Val Ala Val Lys Ala Pro Gly
290                 295                 300

Phe Gly Asp Asn Arg Lys Asn Gln Leu Lys Asp Met Ala Ile Ala Thr
305                 310                 315                 320

Gly Gly Ala Val Phe Gly Glu Glu Gly Leu Thr Leu Asn Leu Glu Asp
            325                 330                 335

Val Gln Pro His Asp Leu Gly Lys Val Gly Glu Val Ile Val Thr Lys
            340                 345                 350

Asp Asp Ala Met Leu Leu Lys Gly Lys Gly Asp Lys Ala Gln Ile Glu
            355                 360                 365

Lys Arg Ile Gln Glu Ile Ile Glu Gln Leu Asp Val Thr Thr Ser Glu
370                 375                 380

Tyr Glu Lys Glu Lys Leu Asn Glu Arg Leu Ala Lys Leu Ser Asp Gly
385                 390                 395                 400

Val Ala Val Leu Lys Val Gly Gly Thr Ser Asp Val Glu Val Asn Glu
            405                 410                 415

Lys Lys Asp Arg Val Thr Asp Ala Leu Asn Ala Thr Arg Ala Ala Val
            420                 425                 430

Glu Glu Gly Ile Val Leu Gly Gly Gly Cys Ala Leu Leu Arg Cys Ile
            435                 440                 445

Pro Ala Leu Asp Ser Leu Thr Pro Ala Asn Glu Asp Gln Lys Ile Gly
450                 455                 460

Ile Glu Ile Ile Lys Arg Thr Leu Lys Ile Pro Ala Met Thr Ile Ala
465                 470                 475                 480

Lys Asn Ala Gly Val Glu Gly Ser Leu Ile Val Glu Lys Ile Met Gln
            485                 490                 495

Ser Ser Ser Glu Val Gly Tyr Asp Ala Met Ala Gly Asp Phe Val Asn
            500                 505                 510

Met Val Glu Lys Gly Ile Ile Asp Pro Thr Lys Val Val Arg Thr Ala
            515                 520                 525

Leu Leu Asp Ala Ala Gly Val Ala Ser Leu Leu Thr Thr Ala Glu Val
530                 535                 540

Val Val Thr Glu Ile Pro Lys Glu Glu Lys Asp Pro Gly Met Gly Ala
545                 550                 555                 560

Met Gly Gly Met Gly Gly Gly Met Gly Gly Gly Met Phe
            565                 570

<210> SEQ ID NO 2
<211> LENGTH: 24
<212> TYPE: PRT
<213> ORGANISM: Homo sapien

<400> SEQUENCE: 2

Val Leu Gly Gly Gly Cys Ala Leu Leu Arg Cys Ile Pro Ala Leu Asp
1               5                   10                  15

Ser Leu Thr Pro Ala Asn Glu Asp
            20

<210> SEQ ID NO 3
```

```
<211> LENGTH: 24
<212> TYPE: PRT
<213> ORGANISM: Homo sapien

<400> SEQUENCE: 3

Val Leu Gly Gly Gly Val Ala Leu Leu Arg Val Ile Pro Ala Leu Asp
1               5                   10                  15

Ser Leu Thr Pro Ala Asn Glu Asp
            20

<210> SEQ ID NO 4
<211> LENGTH: 12
<212> TYPE: PRT
<213> ORGANISM: Homo sapien

<400> SEQUENCE: 4

Ala Leu Leu Arg Val Ile Pro Ala Leu Asp Ser Leu
1               5                   10

<210> SEQ ID NO 5
<211> LENGTH: 12
<212> TYPE: PRT
<213> ORGANISM: Homo sapien

<400> SEQUENCE: 5

Ala Leu Leu Arg Val Ile Pro Ala Leu Asp Ser Leu
1               5                   10

<210> SEQ ID NO 6
<211> LENGTH: 14
<212> TYPE: PRT
<213> ORGANISM: Homo sapien

<400> SEQUENCE: 6

Val Leu Gly Gly Gly Ser Ala Leu Leu Arg Ser Ile Pro Ala
1               5                   10

<210> SEQ ID NO 7
<211> LENGTH: 9
<212> TYPE: PRT
<213> ORGANISM: Homo sapien

<400> SEQUENCE: 7

Ser Ala Leu Leu Arg Ser Ile Pro Ala
1               5

<210> SEQ ID NO 8
<211> LENGTH: 9
<212> TYPE: PRT
<213> ORGANISM: Homo sapien

<400> SEQUENCE: 8

Val Ala Leu Leu Arg Val Ile Pro Ala
1               5

<210> SEQ ID NO 9
<211> LENGTH: 13
<212> TYPE: PRT
<213> ORGANISM: Homo sapien

<400> SEQUENCE: 9

Gly Gly Val Thr Leu Leu Asn Ala Ala Pro Ala Leu Asp
1               5                   10
```

HSP PEPTIDES AND ANALOGS FOR MODULATION OF IMMUNE RESPONSES VIA ANTIGEN PRESENTING CELLS

CROSS-REFERENCE TO RELATED APPLICATIONS

This application is a continuation of International application PCT/IL03/00078 filed Jan. 30, 2003, and claims the benefit of U.S. provisional application No. 60/352,594 filed Jan. 31, 2002, the entire content of each of which is expressly incorporated herein by reference thereto.

FIELD OF THE INVENTION

The present invention relates to peptides and peptide analogs of heat shock proteins (Hsp) capable of interacting directly with dendritic cells. The present invention further relates to pharmaceutical compositions comprising dendritic cells exposed to such peptides and analogs, useful for prevention or treatment of either inflammatory disorders and autoimmune diseases or malignancies, viral infections and allergy.

BACKGROUND OF THE INVENTION

Heat Shock Proteins Heat shock proteins (hsp) are ubiquitous polypeptides produced by all cells of all species. They are among the best-conserved proteins phylogenetically, with respect to both sequence and function. Human and bacterial Heat shock proteins are more than 50% homologous (Jindal et AL. Mol Cell Biol. 9: 2279, 1989). Heat shock proteins are expressed both as constitutive proteins that act as molecular chaperones (Becker J. and Craig A. E., Eur. J. Biochem. 219; 11, 1994), and as inducible stress proteins.

Hsp60 is a mitochondrial chaperone with a major role in protein folding and unfolding as well as translocation of proteins into mitochondria. Hsp60 is found in the cell cytosol under stressful and inflammatory conditions; infection or elevated cytokine levels will induce the cellular stress response. Therefore, it is not surprising that hsp60 is a highly immunogenic protein: it is the "common antigen" of gram-negative bacteria.

Immunological reactivity to both bacterial and autologous-hsp60 is highly prevalent in the general population, since the pathogen-directed immune response can easily convert into an autoimmune response due to the high homology.

T-cell responses to multiple hsp60 epitopes are present in various autoimmune and inflammatory diseases (Van Eden et al. Immunology Today 19; 303, 1998), including type 1 diabetes (Elias et al. Proc. Natl. Acad. Sci. 88: 3088, 1991), rheumatoid and juvenile arthritis, multiple sclerosis, ankylosing spondylitis, pelvic inflammation-associated infertility, inflammatory bowel disease, atherosclerosis, graft rejection and more. The immune system reacts to hsp60 epitopes that are either cross-reactive between the human and bacterial analogues, or idiosyncratic.

Inflammatory diseases associated with hsp60 expression in target tissues include: (i) Autoimmune diseases: diabetes (Birk et al. Proc Natl Acad Sci 93: 1032, 1996), multiple sclerosis, rheumatoid arthritis (Van Eden et al., Nature, 331: 171, 1988), juvenile chronic arthritis; (ii) Chronic inflammation: inflammatory bowel disease, reactive arthritis; (iii) Graft rejection: Hsp60 can contribute significantly to the inflammatory process that ends in graft rejection. By introducing hsp60-derived antagonists at an early stage after transplantation, one could dampen the inflammation and prolong graft survival (Birk et al. Proc Natl Acad Sci, 96: 5159, 1999); (iv) Atherosclerosis: Hsp60 has been implicated in atherosclerosis, since autoantibodies to human hsp60 were demonstrated to correlate with the clinical status of patients and experimental animal models. Moreover, hsp60 can stimulate macrophage functions relevant to atherosclerosis, such as the production of TNFα, IL-6 and matrix-degrading metalloproteinases (Chen et al., J. Immunol. 162, 3212, 1999).

Use of Heat Shock Proteins in Therapy

Many disclosures claim uses of heat shock proteins or fragments thereof as immune modulators in diagnosis, treatment or prevention of autoimmune diseases. Most of these disclosures relate to heat shock protein 60 also known previously as hsp65, or fragments of this protein.

For example, the particular protein produced by the human body during development of IDDM, which serves as a diagnostic marker for the incipient outbreak of IDDM, is the human heat shock protein having a size of about 65 KD (human hsp65) or an antigen cross-reactive therewith as disclosed in EP 0417271, and in U.S. Pat. Nos. 5,114,844; 5,671, 848; 5,578,303 and 5,780,034. It has been disclosed that fragments of this hsp60 protein may serve as therapeutically useful entities in preventing or alleviating IDDM and host vs. graft disease (U.S. Pat. Nos. 6,180,103 and 5,993,803 and WO 96/19236, WO 97/01959 and WO 98/08536).

In addition, fragments of hsp60 may be used as carriers for development of synthetic vaccines by increasing the immunogenicity of poorly immunogenic antigens as disclosed in U.S. Pat. Nos. 5,736,146 and 5,869,058.

European Patent No. 0262710 discloses polypeptides useful for alleviation, treatment, and diagnosis of autoimmune arthritis and similar autoimmune diseases. The claimed polypeptides are derived from bacterial protein named "Antigen A" which was identified later as mycobacterial hsp60.

WO 92/04049 discloses peptides of at least seven amino acids homologous to a fragment of *Mycobacterium tuberculosis* hsp60, which inhibit T-lymphocytes activation and proliferation and can protect from immune reactions and immune-related disease.

WO 89/12455 and WO 94/29459, disclose the use of stress proteins and analogs for producing or enhancing an immune response or for inducing immune tolerance, for prophylaxis or therapy of autoimmune diseases and for treating or preventing infectious or cancers. A fusion protein is claimed comprising a stress protein fused to a protein against which an immune response is desired.

WO 95/25744 discloses microbial stress protein fragments containing epitopes homologous to related mammalian epitopes—used to treat and prevent inflammatory autoimmune diseases and to prevent transplant rejection. The protective epitopes are located in short peptides comprising 5-15 amino acid sequences regions of stress proteins, that are highly conserved between microorganisms and animals.

WO 97/11966 and WO 96/10039 disclose polypeptides of up to 21 amino acids, derived from microbial heat shock protein which are useful for prophylaxis or treatment of autoimmune diseases especially arthritis.

WO 96/16083 discloses a peptide 25 amino acids long, derived from the 10 kD heat shock protein (hsp10) of *Mycobacterium tuberculosis* which is useful in pharmaceutical products for the treatment of inflammatory pathologies, especially rheumatoid arthritis.

WO 91/02542 discloses the use of antigenic and/or immuno-regulatory material derived from *mycobacterium* vaccae and specifically hsp60, for treating chronic inflammatory disorders caused or accompanied by an abnormally high release of IL-6 and/or TNFα.

WO 96/18646 discloses peptides of 9-20 amino acids derived from Mycobacterial hsp60 used for treatment or prevention of autoimmune CNS diseases, e.g. multiple sclerosis, chronic inflammatory CNS disease and primary brain tumors.

WO 94/02509 discloses peptides of 7-30 amino acids derived from DR3-restricted epitope of Mycobacterial hsp60 used for treatment of HLA-DR3 related autoimmune diseases.

WO 00/27870 discloses peptides derived from Mycobacterial and rat hsp60 and vaccines comprising such peptides for immunization against autoimmune and inflammatory diseases.

U.S. Pat. No. 5,958,416 describes heats shock protein peptides and methods for modulating autoimmune central nervous system diseases.

WO 01/43691 discloses fragments and antagonists of Hsp60, capable of reducing or prevention the induction of a pro-inflammatory immune response of cells of the innate immune system by hsp60, for treatment of inflammatory and autoimmune diseases. The compounds disclosed inhibit the binding of hsp60 to the toll-like-receptor, and therefore reduce or prevent the induction of a consequent pro-inflammatory response.

Additional heat shock proteins, other than hsp60, have been disclosed as useful for treatment. For example, U.S. Pat. No. 5,348,945 discloses a method for reducing mortality in stressed tissue with heat shock protein for treatment of atherosclerosis, arterial restenosis and anoxic nerve damage using exogenous hsp70. Other inventions (e.g. JP 10212230, JP 09241159) disclose synthetic and natural compounds and extracts which inhibit the expression of proteins belonging to the hsp60 or hsp27 families and are therefore useful for treating autoimmune diseases and cancers.

Srivastava and colleagues have disclosed use of non-covalent complexes of hsp70, hsp90 or hsp96 together with an antigen for preventing and treating cancer and infectious diseases and for treatment of autoimmune diseases such as diabetes and multiple sclerosis. U.S. Pat. No. 6,322,790 discloses compositions and methods for eliciting an immune response using heat shock protein-peptide complexes in combination with adoptive immunotherapy, for prevention and treatment of neoplastic diseases and infectious diseases. In these methods the complex consists of a heat shock protein non-covalently bound to an antigenic molecule in combination with administering antigen presenting cells sensitized with complexes of hsps non-covalently bound to an antigenic molecule.

Toll Proteins and hsp60

It was recently discovered that hsp60 is a putative endogenous activator of Toll-like receptors in mammals (Ohashi et al. J. Immunol. 164, 558-61, 2000), while the previously described ligands for Toll-like receptors in mammalian cells are of microbial origin, which is in line with a function of these receptors in innate immune responses. This funding suggests that Toll-like receptors may not only have a function in innate immune defense against microbial pathogens but also serve physiological functions by interacting with endogenous ligands.

It is noteworthy that both Toll-like receptors and hsp60 are found early in phylogeny and both are of remarkably conserved structure. This suggested that their interaction is relevant and may also occur in more primitive organisms. Mammalian hsp60 usually is sequestered to the cell interior, in accordance with its ability to function as a chaperone. However, hsp60 becomes accessible when it is set free during necrosis of tissue during inflammation or when hsp60 is partially translocated to the plasma membrane in response to diverse types of stress. It was therefore proposed that autologous hsp60 may serve as a danger signal antigen to the innate immune system (Chen et al. ibid).

Cells of the Adaptive Immune System

The adaptive immune response plays a critical role in the eradication of pathogens. However, inappropriate responses to infection can cause severe pathology. The cells of the adaptive immune system are normally present as circulating cells in the blood and lymph, in an anatomically defined collection of lymphoid organs, and as scattered cells in virtually all tissues. The ability of the adaptive immune system to optimally perform its protective function is dependent on several properties of its constituent cells and tissues. The structure and function of the immune system is reviewed by Abbas et al. Cellular and Molecular immunology, Fourth Edition 2000, W. B. Saunders Company, Philadelphia.

Dendritic Cells and their Role in Immunity

Dendritic cells (DCs) are a family of bone marrow derived antigen-presenting cells (APCs) with an exquisite capacity to interact with T cells and modulate their responses. DCs patrol most non-lymphoid organs including epithelia (e.g. the skin and the mucosa of the intestines where DCs are called Langerhans cells (LCs)), the dermis and the interstitia of vascularized organs such as the heart and kidneys. DCs are also found in the blood and lymph and are present in all lymphoid organs. In the T cell areas of the lymphoid organs they are called interdigitating DCs. DCs from non-lymphoid tissues can migrate to secondary lymphoid organs, via the blood or lymph, bringing antigens to naive T cells from peripheral sites to which the latter cells are excluded. As a very generalized rule, if the DC presenting the antigen to the naive T cell is non-activated, the T cell will be tolerogenic. If the DC presenting the antigen to the naive T cell is activated then the T cell will be stimulated to produce a response. In other words, the first critical decision regulating the response of the immune system depends on whether or by what the dendritic cell has been activated.

The involvement of the heat shock proteins in modulation of immune responses is now well established, however, nowhere in the background art is it taught or suggested that exposure of dendritic cells to Hsp proteins alone (in the absence of antigen) or to isolated Hsp derived peptides can directly regulate the immune response, and that peptides and analogs of heat shock proteins may act directly at the dendritic cell level thereby leading to discrimination between Th1 and Th2 subsets of T cells.

SUMMARY OF THE INVENTION

According to one aspect of the invention it is now disclosed that exposure of antigen presenting cells, particularly dendritic cells, to heat shock proteins themselves even in the absence of antigen, or to peptides or peptide analogs derived from Hsps will enable these antigen presenting cells to activate T cells to produce immunomodulatory cytokines.

The present invention is based on part on the unexpected discovery that certain peptide epitopes derived from hsp60 do not exert their effect as heretofore believed by acting at the level of the T helper cells. Rather it is now disclosed that these epitopes efficiently evoke their immunomodulatory action via the antigen presenting cells.

The present invention discloses certain novel compounds and compositions capable of acting directly on dendritic cells or other antigen presenting cells and thereby to activate other cell types of the immune system. The present invention further discloses known compounds and compositions that may advantageously be used in combination with antigen presenting cells.

According to another aspect of the invention it is now disclosed that exposure of antigen presenting cells, particularly dendritic cells, to peptides or peptide analogs derived from Hsps will modulate the immunomodulatory cytokines produced by specific T cells.

According to another aspect of the present invention it is now disclosed that APCs exposed to Hsps or Hsp derived peptides can subsequently activate specific subsets of T cells to produce immunomodulatory cytokines.

According to yet another aspect of the invention it is now disclosed that APCs, upon exposure to Hsps or Hsp derived peptides directly produce cytokines or chemokines, which affect the behavioral response of T cells. For example T cell adhesion or chemotaxis can be induced or modified by the secreted cytokines or chemokines.

According to another aspect of the present invention, exposure of APCs to Hsps or Hsp derived peptides leads to maturation of APCs and increased expression of cell surface antigens, which are essential to antigen presentation. The presence of certain cell surface antigens is essential for antigen presentation to result in an immune response.

According to one embodiment of the present invention it is disclosed that antigen presenting cells, particularly dendritic cells can serve as the basis for a screening assay to identify novel Hsp derived peptides useful for diagnosis, prevention or therapy. The screening assay comprises the steps of: i) exposing antigen presenting cells, particularly dendritic cells, to the test Hsp derived peptide or peptide analog; ii) washing said cells to remove the test peptides; iii) exposing T cells to said educated antigen presenting cells; iv) measuring the cytokines produced by said T-cells exposed to said antigen presenting cells and to T cell specific antigen; and v) comparing the amount of cytokines produced by T cells exposed to antigen presenting cells not previously exposed to the test peptide.

According to another embodiment, antigen presenting cells, preferably human monocytic cell lines, are tested directly for production of certain cytokines, in response to exposure to Hsp derived peptides or peptide analogs.

A preferred embodiment provides screening assay for identifying an Hsp derived peptide useful for diagnosis or therapy comprises the steps of: (i) exposing antigen presenting cells, particularly dendritic cells, to the test Hsp derived peptide or peptide analog; (ii) measuring the cytokines produced; and (iii) comparing the amounts of cytokines secreted to the amounts secreted from antigen presenting cells not previously exposed to said peptide or peptide analog.

Yet, another embodiment for identifying an Hsp derived peptide useful for diagnosis or therapy provides screening assay comprises the steps of: (i) culturing antigen presenting cells, particularly dendritic cells, with GM-CSF and IL-4; (ii) exposing said cells to a stimulant selected from LPS, zymosan, and a Hsp derived peptide or peptide analog; (iii) measuring the cytokines produced and comparing the amounts of cytokines secreted from antigen presenting cells exposed to said test peptide and antigen presenting cell exposed to LPS or zymosan; or (iv) measuring the amount of surface antigens expressed on said cells and comparing the amounts of surface antigens expressed on antigen presenting cells exposed to said the test peptide and antigen presenting cell exposed to LPS or zymosan.

According to another embodiment of the present invention, exposure of the APCs to Hsps or Hsp derived peptides gives rise to a subsequent Th2 response.

According to yet another embodiment, exposure of the APCs exposed to Hsps or Hsp derived peptides gives rise to a subsequent Th1 response.

Preferably exposure of the DCs is performed in vitro or ex vivo. Alternatively and preferably DCs exposed to the Hsps or DCs exposed to the Hsp derived peptide or peptide analog may be injected into an animal, preferably a human, in order to elicit the desired immune response.

According to one embodiment, the antigen presenting cells are dendritic cells, more preferably the APCs are autologous DCs.

Another preferred embodiment of the invention provides pharmaceutical compositions comprising a peptide analog according to the invention. These pharmaceutical compositions comprise at least one peptide analog of a heat shock protein. The formulation of said compound into a pharmaceutical composition further comprises the addition of a pharmaceutically acceptable carrier, excipient and/or diluent.

The present invention further provides pharmaceutical compositions comprising a Heat shock protein derived peptide or an analog of said peptide together with antigen presenting cells, preferably dendritic cells, more preferably autologous dendritic cells.

The present invention further provides pharmaceutical compositions consisting essentially of a Heat shock protein and antigen presenting cells. These compositions and methods of using them are distinct from the background art in that they do not require or comprise an antigenic molecule other than the Hsp itself. Preferably, the Heat shock protein for use in pharmaceutical compositions in conjunction with antigen presenting cells is Hsp60, though Hsp70, Hsp90 and Hsp 96 may be used as well. Additionally and preferably the APCs are dendritic cells. Additionally and preferably the antigen presenting cells are autologous.

The peptide analogs of the present invention are useful as active ingredients in pharmaceutical compositions for the prevention or treatment of diseases involving abnormal Th1 or Th2 levels response in their etiology or pathology.

One embodiment of the present invention provides Hsp peptides that are useful in suppression or prevention of certain diseases and conditions in which stimulation of Th2 response is beneficial, such as chronic inflammatory diseases, graft rejection and certain autoimmune diseases.

Another embodiment provides other Hsp peptides according to the present invention, that are identified as Th1 stimulators, useful as active ingredients in pharmaceutical compositions for the prevention or treatment of cancer, allergy and parasitic diseases.

Yet another embodiment provides methods for diagnosis or monitoring the progression of these diseases using the Hsp peptides of the present invention.

A preferred embodiment of the present invention provides methods of treatment of an individual in need thereof by administering pharmaceutical compositions comprising Hsp peptides and analogs.

According to another currently preferred embodiment pharmaceutical compositions comprising DCs exposed to Hsps are administered to an individual in need thereof.

These pharmaceutical compositions may be administered by any suitable route of administration, including orally, topically, transdermally or systemically. Preferred modes of administration include but are not limited to parenteral routes such as intravenous and intramuscular injections. For the pharmaceutical compositions comprising cells, parenteral routes of administration are generally required. However for pharmaceutical compositions comprising peptides without cells, additional preferred routes of administration include but are not limited to administration via nasal inhalation or oral ingestion.

One currently preferred embodiment of the invention provides Hsp derived peptides obtained by screening assays on APCs.

Disclosures in the background art relate to numerous specific peptides derived from hsp60, which are useful in the treatment of specific diseases or disorders based on the interaction of those peptides with specific T-cell receptors. These disclosures are directed to peptides derived from hsp60 which are useful for the suppression or prevention of immune responses mediated by other cells of the immune system, e.g. T-cells or cells of the innate immunity. The present application discloses peptides and analogs derived from hsp60 acting at the dendritic cell level, and encompasses known hsp60 peptides previously claimed for their capacity to modulate the immune responses now shown to act via APCs. It is explicitly to be understood that the known peptides themselves are excluded from the present invention. However, compositions comprising these known peptides or analogs together with antigen presenting cells, particularly dendritic cells are within the scope of the present invention.

The present invention is exemplified hereinbelow for the known peptide p277(Val$^6$-Val$^{11}$), also known as DiaPep277, disclosed in U.S. Pat. No. 6,180,103, though this is for illustrative purposes only. Novel fragments and analogs of said peptide are now disclosed as being identified by methods according to the invention. Further embodiments provide pharmaceutical compositions comprising said novel fragments and analogs of DiaPep277 together with antigen presenting cells, particularly dendritic cells, preferably autologous dendritic cells. Further embodiments provide methods for prevention or treatment of diseases involving abnormal Th1 or Th2 levels, such as autoimmune, inflammatory, allergic viral infections and malignancies, using pharmaceutical compositions comprising fragments and analogs of p277 (Val$^6$-Val$^{11}$).

BRIEF DESCRIPTION OF THE DRAWINGS

The invention will better be understood in relation to the drawings and detailed description of the preferred embodiments which follow.

DETAILED DESCRIPTION OF THE INVENTION

Figure 1:
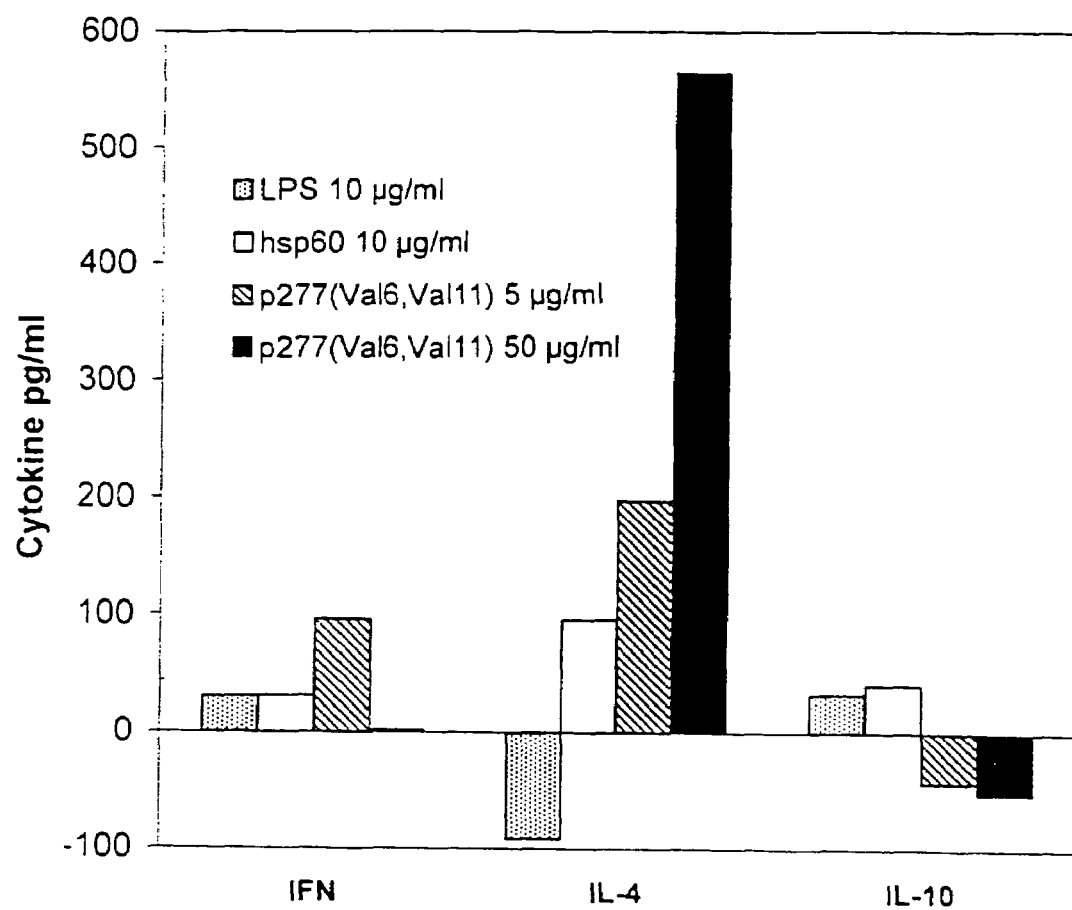
FIG. 1 demonstrates the effect of p277(Val$^6$-Val$^{11}$) on T cells cytokine profile after incubation of the compound with dendritic cells.

The present invention is based on part on the unexpected discovery that certain peptide epitopes derived from hsp60 (Seq ID No. 1) do not exert their effect as heretofore believed by acting solely at the level of the T helper cells. Rather it is now disclosed that these epitopes efficiently evoke their immunomodulatory action via the antigen presenting cells.

The present invention discloses certain novel compounds and compositions capable of acting directly on dendritic cells or other antigen presenting cells and thereby activating other cell types of the immune system. The present invention further discloses known compounds and compositions that may advantageously be used in combination with antigen presenting cells.

Specific novel peptides according to the present invention are exemplified by fragments of p277(Val$^6$-Val$^{11}$), also known as DiaPep277, disclosed in U.S. Pat. No. 6,180,103. Said fragments were identified by the methods of the present invention. Also disclosed are pharmaceutical compositions comprising antigen presenting cells exposed to these peptides. Use of the pharmaceutical composition for the prevention or treatment of diseases involving abnormal Th1 or Th2 levels are is disclosed.

The present invention further relates to pharmaceutical compositions comprising an Hsp derived peptide according to the invention. The formulation of said compound into a pharmaceutical composition further comprises the addition of a pharmaceutically acceptable carrier, excipient and/or diluent The pharmaceutical compositions according to the present invention comprise at least one peptide derived from heat shock protein or an analog thereof. These pharmaceutical compositions may be administered by any suitable route of administration, including orally, topically, transdermally or systemically. Preferred modes of administration include but are not limited to parenteral routes such as intravenous and intramuscular injections. Additional preferred routes of administration include but are not limited to administration via nasal inhalation or oral ingestion.

The novel peptides of the present invention are useful as active ingredients in pharmaceutical compositions for the prevention or treatment of diseases involving abnormal Th1 or Th2 levels response in their etiology or pathology. In this respect it is an object of the present invention to provide methods of using these peptides for suppression or prevention of certain diseases and conditions in which stimulation of Th2 response is beneficial, such as chronic inflammatory diseases, graft rejection and autoimmune diseases. Alternatively, other peptides according to the present invention, that are identified as Th1 stimulators may be useful as active ingredients in pharmaceutical compositions for the prevention or treatment of cancer, allergy and parasitic diseases. Methods for diagnosis or monitoring the progression of these diseases using peptides according to the invention are also within the scope of the invention.

Peptide analogs of the present invention and pharmaceutical compositions comprising them, are useful in methods for the treatment of disorders including: chronic inflammatory diseases autoimmune diseases, graft rejection, and infectious diseases including but not limited to type I diabetes, rheumatoid arthritis, reactive arthritis, juvenile chronic arthritis, multiple sclerosis, myasthenia gravis, systemic lupus erythematosus, Crohn's disease, inflammatory bowel disease, atherosclerosis, gingivitis, arterial restenosis, anoxic nerve damage, primary biliary cirrhosis, sarcoidosis, ulcerative colitis, psoriasis, Guillain-Barre syndrome, and neuro-inflammatory diseases, as well as disorders including cancer, allergy and parasitic diseases.

WO 01/43691 discloses methods for identifying, screening and characterizing compounds which can act as antagonists of hsp60 based on the finding that hsp60 binds to the Toll-like receptor 4 complex and as a result elicits a potent pro-inflammatory response in cells of the innate immune system. The screening system disclosed therein is thus based on inhibition of hsp60 binding to lymphatic cells, preferably macrophages, expressing Toll-like receptor. The present invention is directed to the action of hsp60 peptides on the dendritic cell level. The expected effect is a direct effect on the dendritic cells and not an inhibition effect. The "educated" dendritic cells subsequently deliver the signal to the T-cells.

Heat Shock Proteins and Immunomodulation

Heat shock proteins have a critical and central role in initiation or modulation of immune responses. According to the self/non-self model of Janeway (Janeway et al. Proc. Nat. Acad. Sci. 98, 7461-7468, 2001), the heat shock proteins (notably hsp60) have strong homology to bacterial proteins. In the danger theory (Colin C. A. and Matzinger P. Seminars in Immunology 12, 231-238, 2001) it is obvious that cells "in danger" have increased levels of heat shock proteins and that they are one of the obvious signs of cellular distress.

Having activated the dendritic cell, the immune system is primed to respond to the antigens carried back to the T cells by the dendritic cell returning from the periphery. The next decision is the type of response to be mounted. T cells that are CD8+, mount a cytotoxic cell response. T cells that are CD4+ are responsible for the T helper response. The CD4+ T helper cells can be divided into distinct subsets depending on the kind of lymphokines they produce. Th1s secrete IL-2, IFNγ, and TNFα, whereas Th2s secrete IL-4, IL-5, IL-10 and IL-13. Th1s predominantly control cell-mediated immune responses and appear to be involved in chronic inflammatory conditions, whereas Th2s inhibit the Th1 response while upregulating IgE production and are prominent in the pathogenesis of allergic and parasitic diseases. Both types of T cells are derived from naive T cells and in vitro the type of response can be influenced by addition of cytokines to the responding cells. In general, Th1 cytokines such as IL-2 promote a Th1 response and Th2 cytokines such as IL-4 promote a Th2 response. The trigger for the initial commitment to the type of response has not been definitively shown. To move the problem back one step, it has been reported that dendritic cells can be divided into DC1 and DC2 responsible for influence on Th1 and Th2 type responses respectively. However the trigger for the initial commitment of the dendritic cells is also not known.

The peptide designated p277(Val$^6$-Val$^{11}$) is a linear 24-residues-long analog corresponding to residues 436-460 of human hsp60. The peptide, disclosed in U.S. Pat. No. 6,180,103, was identified as a therapeutically useful entity in preventing or alleviating IDDM and graft rejection. The peptide was thought to act by influencing the type of Th response in favor of Th2 type. It was now unexpectedly found that the peptide acts directly at the level of the dendritic cells. Exposure to p277(Val$^6$-Val$^{11}$) greatly increased the IL4 response of T cells stimulated by the "educated" dendritic cells.

HSP Peptides and the Innate Immune System

Several approaches were applied to investigate the effect of the compositions of the present invention on the human innate system.

a. T cells stimulated with "educated" dendritic cells exposed to tested compounds were tested for their influence on IL4 response.

b. Mouse macrophage cell line was tested for influence on nitric oxide production after stimulation with the compounds of the present invention.

c. Peripheral blood derived dendritic cells, which are activated differentially through Toll-like receptor 2 (Tlr2) or Tlr4 were tested for IP-10 and 11-8 secretion after stimulation with the compounds of the present invention. These cells were also used for testing the effects of the compositions on dendritic cells maturation as manifested by expression of CD86.

d. Peripheral blood monocytes with or without preincubation with the tested compounds were tested for influence on the amount of IP-10 produced in response to stimulus with LPS.

e. Differentiated human monocytic cell lines either direct stimulated with the tested compound or preincubated and then stimulated with LPS, were tested for influence on the amount of secreted TNF, or IP-10.

f. Mouse macrophage cell lines were tested for influence on nitric oxide production after stimulation with the compounds of the present invention.

The effect of the compositions of the present invention on peripheral blood derived dendritic cells, was tested according to a protocol described by Re, F. and Strominger, J. L. 2001. Toll-like receptor 2 (Tlr2) and Tlr4 differentially activate human dendritic cells. (J Biol Chem 276: 37692-9). According to this method immature dendritic cells derived from human peripheral blood are used. The outcome after incubating the cells with tested molecules is different if the stimulation is through the Toll 4 receptor or the Toll 2 receptor. According to the authors, Toll 2 signaling by stimulation with zymosan is associated with a Th2 kind of response (exemplified by IL-8) and Toll 4 signaling, such as obtained by LPS stimulation (exemplified by IP-10), with a Th1 type of response. The compositions of the present invention were tested using a similar assay system in order to check which stimulation type they induce. It was now found that cell maturation is increased after stimulation with LPS, zymosan or p277(Val$^6$-Val$^{11}$). The indication that out of the cytokines secreted, p277(Val$^6$-Val$^{11}$) stimulation resulted in IL-8 secretion but no IP-10 secretion, may suggest that p277(Val$^6$-Val$^{11}$) similar to zymosan, stimulates through the Toll 2 receptor. The increase in CD86 expression after exposure of APCs to Hsps or Hsp derived peptides is important since CD86 (B7.2) is an essential component of the immunological synapse formed between T cells and APC. This synapse consists of CD80 and CD86 on the side of the APC and CD28 and CD40 on the side of the T cell. T cell recognition of peptide on APC without the concurrent expression of CD86 gives rise to anergy instead of a T cell response. Therefore in order to produce a response all components must be present.

The effects of the compound of the present invention on peripheral blood monocyes were tested. Results show that while direct stimulation with the test compounds did not give rise to IP-10, preincubation with the tested compound did increase the IP-10 response to stimulation with LPS. Stimulation with Hsp60 with or without preincubation did not generate IP-10. This indicates direct effect of the test compounds on monocytes, which affects their response to another stimulus (such as LPS).

The direct effects of Hsp peptides and analogs according to the present invention on APCs were further evidenced in human cell lines. Differentiated human monocytic cells incubated with hsp60 peptide analog did not secrete TNF, or IP-10 directly. However, preincubation with the peptide analogs and subsequent stimulus with LPS gave rise to an increased amount of IP-0 secreted as compared to LPS alone. These results further indicate the direct effects of Hsp peptides and analogs according to the present invention on APCs.

Terminology and Definitions:

The term "heat shock protein" relates to any member of heat shock proteins family also known as chaperones. The term "heat shock protein" also referred to "stress protein" a term that was used in the past to such molecules.

The term "fragment" in the context of the present invention preferably means a part of hsp molecule which comprises at least 5, more preferably at least 7 consecutive amino acids in a sequence as it occurs in a native hsp or to a part of an hsp molecule which may be obtained by clearing an hsp60 protein, e.g., enzymatically or by other means. In this case the fragment does not necessarily have to contain only a consecutive amino acid sequence, but may contain two or more of such sequences which can be linked to each other, e.g., by disulfide bonds, by peptide bonds or by any other covalent bond.

As used herein "peptide" indicates a sequence of amino acids linked by peptide bonds. The peptides according to the present invention comprise a sequence of 5 to 30 amino acid residues, preferably 6 to 24 residues, more preferably 7 to 18 amino acids. A peptide analog according to the present invention may optionally comprises at least one bond which is an amide-replacement bond such as urea bond, carbamate bond, sulfonamide bond, hydrazine bond, or any other covalent bond.

Whenever "peptide of the invention" or "analogs of the invention" are mentioned in the present specification and claims, also salts, conservatively modified variants, functional peptides and functional derivatives thereof are contemplated, as long as the biological activity of the peptide is maintained.

"Functional derivatives" of the peptides of the invention as used herein covers derivatives which may be prepared from the functional groups which occur as side chains on the residues or the N- or C-terminal groups, by means known in the art, and are included in the invention as long as they remain pharmaceutically acceptable, i.e., they do not destroy the activity of the peptide, do not confer toxic properties on compositions containing it and do not adversely affect the antigenic properties thereof.

These derivatives may, for example, include aliphatic esters of the carboxyl groups, amides of the carboxyl groups produced by reaction with ammonia or with primary or secondary amines, N-acyl derivatives of free amino groups of the amino acid residues formed by reaction with acyl moieties (e.g., alkanoyl or carbocyclic aroyl groups) or O-acyl derivatives of free hydroxyl group (for example that of seryl or threonyl residues) formed by reaction with acyl moieties.

As used herein, "functional" includes reference to an activity sufficient to produce a desired effect. A "functional peptide" will have the activity to achieve a desired result, such as cytokine inhibition or induction. Alternatively, a functional peptide will provide the cell with a beneficial or therapeutic effect, such as induction of release of a specific mediator. Thus reference to a particular peptide or "functional peptide" includes the naturally occurring peptide sequence or a peptide that has the substantially the same activity as the naturally occurring sequence. "Functional peptides" of the invention also include modified peptides (with amino acid substitutions, both conservative and non-conservative) that have the same activity as a wild-type or unmodified peptide. "Salts" of the peptides of the invention contemplated by the invention are physiologically acceptable organic and inorganic salts.

The term "analog" further indicates a molecule which has the amino acid sequence according to the invention except for one or more amino acid changes. Analogs according to the present invention may comprise also peptidomimetics. "Peptidomimetic" means that a peptide according to the invention is modified in such a way that it includes at least one non-coded residue or non-peptidic bond. Such modifications include, e.g., alkylation and more specific methylation of one or more residues, insertion of or replacement of natural amino acid by non-natural amino acids, replacement of an amide bond with other covalent bond. A peptidomimetic according to the present invention may optionally comprises at least one bond which is an amide-replacement bond such as urea bond, carbamate bond, sulfonamide bond, hydrazine bond, or any other covalent bond. The design of appropriate "analogs" may be computer assisted.

As used herein and in the claims, the phrase "therapeutically effective amount" means that amount of peptide or peptide analog or composition comprising same to administer to a host to achieve the desired results for the indications disclosed herein.

Certain abbreviations are used herein to describe this invention and the manner of making and using it. For instance, 2Abu refers to 2-aminobutyric acid, Alloc refer to allyloxycarbonyl, APC refers to antigen presenting cells, Boc refers to the t-butyloxycarbonyl radical, BOP refers to benzotriazol-1-yloxy-tris-(dimethylamino)phosphonium hexafluorophosphate, DC refers to dendritic cells, DIEA refers to diisopropyl-ethyl amine, EDT refers to ethanedithiol, ELISA refers to enzyme-linked immunosorbent assay, FCS refers to fetal calf serum, Fmoc refers to the fluorenylmethoxycarbonyl radical, HBTU refers to 1-hydroxybenztriazolyltetramethyl-uronium hexafluorophosphate, HOBT refers to 1-hydroxybenzotriazole, HPLC refers to high pressure liquid chromatography, Hsp refers to heat shock protein, IDDM refers to Insulin-dependent Diabetes Mellitus, IFN refers to interferon-gamma, IL- refers to interleukin, IP-10 refers to interferon-inducible protein 10, kD refers to Kilo Dalton, LC refers to Langerhans cells, LPS refers to lipopolysaccharide, MPS refers to Multiple parallel synthesis, MS refers to mass spectrometry, NMM refers to N-methylmorpholine, NMP refers to 1-methyl-2-pyrrolidonone, PMA refers to phorbol myristyl acetate, PyBOP refers to Benzotriazole-1-yl-oxy-tris-pyrrolidino-phosphonium hexafluorophosphate, PyBrOP refers to Bromo-tris-pyrrolidino-phosphonium hexafluorophosphate, and TFA refers to trifluoroacetic acid, Tlr refers to toll-like-receptor, Tlr2 refers to Toll-like receptor 2, Tlr4 refers to Toll-like receptor 4, TNF refers to tumor necrosis factor alpha.

The amino acids used in this invention are those which are available commercially or are available by routine synthetic methods. Certain residues may require special methods for incorporation into the peptide, and either sequential, divergent and convergent synthetic approaches to the peptide sequence are useful in this invention. Natural coded amino acids and their derivatives are represented by three-letter codes according to IUPAC conventions. When there is no indication, the L isomer was used. The D isomers are indicated by "D" before the residue abbreviation.

Conservative substitution of amino acids as known to those skilled in the art are within the scope of the present invention. Conservative amino acid substitutions includes replacement of one amino acid with another having the same type of functional group or side chain e.g. aliphatic, aromatic, positively charged, negatively charged. These substitutions may enhance oral bioavailability, penetration into the central nervous system, targeting to specific cell populations and the like. One of skill will recognize that individual substitutions, deletions or additions to peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W). (see, e.g., Creighton, Proteins (1984)).

Screening System using Antigen Presenting Cells

The screening system for testing peptides at the dendritic cell level involves production and education of dendritic cells and subsequent utilization of these educated dendritic cells for stimulation of T-cells. While it is feasible to use other sources including human APC, it is more convenient to perform the screen for candidate peptides or other test compounds using mouse cells.

A particularly convenient source of APC is bone marrow cells from mice transgenic for the TcR. All cells from such mice (DO.11.10 Jackson Labs, Bar Harbor, Me.) respond to a single peptide the OVA peptide (OVA323-329). The nonadherent cells from cultures of these bone marrow cells in the presence of the hemopoietic growth factor GM-CSF serve as immature dendritic cells which are "educated" by exposure to a test compound or peptide.

These educated cells are then cocultured with T cells. Naive T cells are prepared from the spleen cells of the DO.11.10 mice and cultured with the educated dendritic cells in the presence of various concentrations of the OVA peptide.

The cell supernatants are collected and assayed for cytokine content (e.g., Interferon γ, IL-4, IL-10 and IL-12). The patterns of response obtained are used to distinguish the active peptides or test compounds. Peptides that induce Th1 cells are distinguished from those that induce Th2 cells, based on the cytokines produced as known in the art.

Alternatively, APCs exposed to Hsp peptides and analogs are tested for direct influence on cytokine production. For example, pre-monocyte like derived cells (e.g. human monocytic cell line THP-1), which can be differentiated to monocytes by treatment with 100 nM phorbol ester (12-O-tetradecanoylphorbol-13-acetate, PMA) for 72 hours, are used. During PMA treatment the cell's sensitivity to stimulus with LPS and hsp60 increases by more than 100 fold with respect to TNF secretion. Differentiated cells are preincubated with the tested compounds or incubated after PMA treatment following subsequent stimulus with LPS. Secreted amounts of cytokines (such as TNF, and IP-10) are measured. Another example for direct measuring of cytokines secreted from APCs exposed to Hsp peptides and analogs involve measurement of cytokines (e.g. IP-10 and IL-8) secretion in human peripheral blood mononuclear cells cultured first with GM-CSF and IL4 and then with LPS, zymosan or tested peptide. These cells are also used for investigation of cell surface antigens (e.g. CD83 and CD86) indicating their maturation.

Additional Screening Systems

After screening at the dendritic cell level, which identify the compounds with potential activity toward Th2 or Th1 stimulation, and after confirmation of the compound's activity in a specific in-vitro assay, the selected compounds are further tested for anti-inflammatory activity and in several animal models for autoimmune diseases. Examples for such assays and models are: influence on insulitis and diabetes in mouse models, as described in WO 96/19236 and WO 97/01959; WO 96/10039 which describes protection against pristane induced arthritis which is an in-vivo model in mice for arthritis; WO 96/16083 which describes an in-vivo method for rheumatoid arthritis model in rat; WO 96/32957 which describes protection against Experimental Allergic Encephalomyelitis (EAE) which is an in-vivo model (in rodents) for multiple sclerosis; and U.S. Pat. No. 5,348,945 which describes an in-vivo model for testing the effect of the compounds on atherosclerosis. A detailed example for testing the compounds and compositions of the present invention in animal model of Crohn's disease is described in example 10 hereinafter.

Combination with Adoptive Immunotherapy

Adoptive immunotherapy refers to a therapeutic approach for treating cancer or infectious diseases in which immune cells are administered to a host with the aim that the cells mediate either directly or indirectly specific immunity to tumor cells and/or antigenic components or regression of the tumor or treatment of infectious diseases, as the case may be. (See U.S. Pat. No. 5,985,270) In accordance with the methods described herein, APC are sensitized with hsp peptides and used in adoptive immunotherapy. The hsp peptide-sensitized APC can be administered concurrently with hsp-peptide, or before or after administration of hsp-peptide. Furthermore, the mode of administration can be varied, including but not limited to, e.g., subcutaneously, intravenously, intraperitoneally, intramuscularly, intradermally or mucosally.

Target Autoimmune Diseases

Autoimmune diseases that can be treated by the methods of the present invention include, but are not limited to, insulin dependent diabetes mellitus (i.e., IDDM, or autoimmune diabetes), multiple sclerosis, systemic lupus erythematosus, Sjogren's syndrome, scleroderma, polymyositis, chronic active hepatitis, mixed connective tissue disease, psoriasis, primary biliary cirrhosis, pernicious anemia, autoimmune thyroiditis, idiopathic Addison's disease, vitiligo, gluten-sensitive enteropathy, Graves' disease, myasthenia gravis, autoimmune neutropenia, idiopathic thrombocytopenia purpura, rheumatoid arthritis, cirrhosis, pemphigus vulgaris, autoimmune infertility, Goodpasture's disease, bulbous pemphigoid, discoid lupus, ulcerative colitis, Crohn's disease and dense deposit disease. The diseases set forth above, as referred to herein, include those exhibited by animal models for such diseases, such as, for example non-obese diabetic (NOD) mice for IDDM and experimental autoimmune encephalomyelitis (EAE) mice for multiple sclerosis.

The methods of the present invention can be used to treat such autoimmune diseases by reducing or eliminating the immune response to the patient's own (self) tissue, or, alternatively, by reducing or eliminating a pre-existing autoimmune response directed at tissues or organs transplanted to replace self tissues or organs damaged by the autoimmune response.

Target Infectious Diseases

Infectious diseases that can be treated or prevented by the methods of the present invention are caused by infectious agents including, but not limited to viruses, bacteria, fungi protozoa and parasites.

Viral diseases that can be treated or prevented by the methods of the present invention include, but are not limited to, those caused by hepatitis type A, hepatitis type B, hepatitis type C, influenza, varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, huntavirus, coxsachie virus, mumps virus, measles virus, rubella virus, polio virus, human immunodeficiency virus type I (HIV-I), and human immunodeficiency virus type U (HIV-II).

Bacterial diseases that can be treated or prevented by the methods of the present invention are caused by bacteria including, but not limited to, mycobacteria rickettsia, mycoplasma, neisseria and legionella.

Protozoal diseases that can be treated or prevented by the methods of the present invention are caused by protozoa including, but not limited to, leishmania, and trypanosoma.

Parasitic diseases that can be treated or prevented by the methods of the present invention are caused by parasites including, but not limited to, chlamydia and rickettsia.

Target Cancers

Cancers that can be treated or prevented by the methods of the present invention include, but not limited to human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease.

In a specific embodiment the cancer is metastatic. In another specific embodiment, the patient having a cancer is immunosuppressed by reason of having undergone anti-cancer therapy (e.g., chemotherapy radiation) prior to administration of the hsp molecule of the invention. In another specific embodiment, the cancer is a tumor.

Prevention and Treatment of Primary and Metastatic Neoplastic Diseases

There are many reasons why immunotherapy as provided by the present invention is desired for use in cancer patients. First, if cancer patients are immunosuppressed and surgery, with anesthesia, and subsequent chemotherapy, may worsen the immunosuppression, then with appropriate immunotherapy in the preoperative period, this immunosuppression may be prevented or reversed. This could lead to fewer infectious complications and to accelerated wound healing. Second, tumor bulk is minimal following surgery and immunotherapy is most likely to be effective in this situation. A third reason is the possibility that tumor cells are shed into the circulation at surgery and effective immunotherapy applied at this time can eliminate these cells.

In a specific embodiment, the preventive and therapeutic methods of the invention are directed at enhancing the immunocompetence of the cancer patient either before surgery, at or after surgery, and to induce tumor-specific immunity to cancer cells, with the objective being inhibition of cancer, and with the ultimate clinical objective being total cancer regression and eradication.

Pharmacology

Apart from other considerations, the fact that the novel active ingredients of the invention are peptides, peptide analogs or cells, dictates that the formulation be suitable for delivery of these type of compounds. Clearly, peptides are less suitable for oral administration due to susceptibility to digestion by gastric acids or intestinal enzymes. The preferred routes of administration of peptides are intra-articular, intravenous, intramuscular, subcutaneous, intradermal, or intrathecal. A more preferred route is by direct injection at or near the site of disorder or disease.

Pharmaceutical compositions of the present invention may be manufactured by processes well known in the art, e.g., by means of conventional mixing, dissolving, granulating, grinding, pulverizing, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active compounds into preparations which, can be used pharmaceutically. Proper formulation is dependent upon the route of administration chosen.

For injection, the compounds of the invention may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants for example polyethylene glycol are generally known in the art.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for the chosen route of administration. For buccal administration, the compositions may take the form of tablets or lozenges formulated in conventional manner.

For administration by inhalation, the variants for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the peptide and a suitable powder base such as lactose or starch.

Pharmaceutical compositions for parenteral administration include aqueous solutions of the active ingredients in water-soluble form. Additionally, suspensions of the active compounds may be prepared as appropriate oily injection suspensions. Suitable natural or synthetic carriers are well known in the art (Pillai et al., Curr. Opin. Chem. Biol. 5, 447, 2001). Optionally, the suspension may also contain suitable stabilizers or agents, which increase the solubility of the compounds, to allow for the preparation of highly concentrated solutions. Alternatively, the active ingredient may be in powder form for reconstitution with a suitable vehicle, e.g., sterile, pyrogen-free water, before use.

The compounds of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of a compound effective to prevent, alleviate or ameliorate symptoms of a disease of the subject being treated. Determination of a therapeutically effective amount is well within the capability of those skilled in the art.

Toxicity and therapeutic efficacy of the peptides described herein can be determined by standard pharmaceutical procedures in cell cultures or experimental animals, e.g., by determining the $IC_{50}$ (the concentration which provides 50% inhibition) and the $LD_{50}$ (lethal dose causing death in 50% of the tested animals) for a subject compound. The data obtained from these cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition (e.g. Fingl, et al., 1975, in "The Pharmacological Basis of Therapeutics", Ch. 1 p. 1).

Depending on the severity and responsiveness of the condition to be treated, dosing can also be a single administration of a slow release composition, with course of treatment lasting from several days to several weeks or until cure is effected or diminution of the disease state is achieved. The amount of a composition to be administered will, of course, be dependent on the subject being treated, the severity of the affliction, the manner of administration, the judgment of the prescribing physician, and all other relevant factors.

Analogs of heat shock proteins constructed based in part on the sequences of a number of known heat shock proteins as presented in the examples below. The following examples are intended to illustrate how to make and use the compounds and methods of this invention and are in no way to be construed as a limitation. Although the invention will now be described in conjunction with specific embodiments thereof, it is evident that many modifications and variations will be apparent to those skilled in the art. Accordingly, it is intended to embrace all such modifications and variations that fall within the spirit and broad scope of the amended claims.

EXAMPLES

General Methods

Production and Education of Mouse Dendritic Cells and Stimulation of T-cells

Whelan et al. (J. Immunol 164, 6453-6460, 2000) addressed the problem in mice by an experiment in which mouse bone marrow cells were grown for 6 days in culture with GM-CSF to give immature dendritic cells. These dendritic cells were then incubated overnight with LPS (known to drive cells to DC1) or with a nematode antigen. The reason for the choice of nematode antigen was that injection of this antigen in vivo gives rise to a Th2 response in animals. After this so-called "education" of the dendritic cells, they were washed and subsequently incubated with naive T cells in the presence of antigenic stimulus. The experiment was possible because of the use of transgenic mice in which all the T cells respond to the same peptide (OVA323-339) which absolves the system from any question of bias of the T cell response at the level of the T cells. Any bias should be a consequence of the "education" of the dendritic cells. After three days of incubation the cytokine responses produced by the T cells, were measured by ELISA. It was found that the LPS incubation gave rise to more IFNγ (Th1) than did either controls or nematode antigen. In contrast, nematode antigen incubation gave rise to more IL-4 (Th2) than did controls while the LPS incubation inhibited the IL4 response. Therefore, the nematode antigen was said to drive cells to DC2. A similar method was used for testing the compounds of the present invention:

1. Bone marrow cells were extracted from the leg bones of DO.11.10 mice transgenic for the TcR. All cells from these mice respond to the OVA peptide (OVA323-329).
2. Bone marrow cells were plated at $10^6$ cells/ml in 100 mm diameter tissue culture petri dishes in Iscove's medium supplemented with 10% FCS, 2 nM L-glutamine, 1 mM sodium pyruvate, penicillin/streptomycin (according to manufacturer's recommendations), non-essential amino acids, 50 µM β-mercaptoethanol and 10 ng/ml mGM-CSF.
3. After 4 days, the medium was carefully removed and replaced with fresh medium
4. After 6 days, the non-adherent cells were harvested and used as immature dendritic cells
5. The immature dendritic cells are plated at $1\times10^6$ cells/ml, 1 ml/well in 24 well plates in the above medium with various reagents added at various concentrations and incubated overnight. This is the stage in which the dendritic cells are "educated"
6. The next day the cells were harvested and washed 3 times then resuspended at $5\times10^4$ cells/ml in 1 ml of the above medium but without the addition of GM-CSF to be coc-ultured with T cells
7. Naive T cells were prepared from the spleen cells of DO.11.10 mice which were harvested and passed over nylon wool columns (according to the manufacturer's recommendations) to select for the non-adherent T cells and then depleted for macrophages taking the cells that did not adhere to plastic after 2 hours.
8. $5\times10^5$ T cells were cultured with the dendritic cells from step 6 in the presence of various concentrations of the OVA peptide (0, 0.3 nM, 3 nM and 30 nM).
9. After 3 days PMA (50 ng/ml) and ionomycin (500 ng/ml) were added to further stimulate the cells.

10. The next day the cell supernatants were collected and assayed for cytokine content (Interferon γ, IL4, IL-10 and IL-12).

Example 1

Influence of p277(Val$^6$-Val$^{11}$) on Cytokines Profile

The compound was tested for stimulation of DO.11.10 bone marrow cells according to the assay described above (Production and education of mouse dendritic cells and stimulation of T-cells).

BALB/c DO.11.10 bone marrow cells were cultured for dendritic cells and then stimulated with LPS 1 μg/ml, LPS 10 μg/ml, hsp60 3 μg/ml, hsp60 10 μg/ml, p277 5 μg/ml and p277 50 μg/ml. The cells were then transferred to wells with T cells from fresh BALB/c DO.11.10 mice and stimulated with OVA peptide at different concentrations (0, 0.3 nM, 3 nM, 30 nM). Supernatant was collected after 48 hours for assay. 30 μl was taken for IFN, 40 μl for IL4 and IL-10 and 50 μl for IL-12 assays. The results are presented in the following tables, as amount of cytokine (pg/ml), and in FIG. 1.

After exposure to p277(Val$^6$-Val$^{11}$), dendritic cells influence T cells to produce more IL-4 than non-exposed dendritic cells. This is characteristic of a Th2 response. This is in contrast to treatment with LPS which results in a characteristic Th1 response with decreased IL4 and increased IFN gamma. Therefore in any disease associated with inflammatory (Th1 type) responses, treatment with hsp60 peptide analogs can modulate the cytokine profile to a non-pathogenic response.

TABLE 1

Cytokines secretion of T cells stimulated with 0.3 nM Ova peptide and educated dendritic cells.

|  | LPS 1 μg/ml | LPS 10 μg/ml | hsp60 3 μg/ml | hsp60 10 μg/ml | p277 (Val$^6$-Val$^{11}$) 5 μg/ml | p277 (Val$^6$-Val$^{11}$) 50 μg/ml | GMCSF alone |
|---|---|---|---|---|---|---|---|
| IFN | 328.33 | 478.89 | 447.78 | 480.56 | 722.22 | 373.89 | 367.78 |
| IL-4 | 11.07 | 1.07 | 35.96 | 24.29 | 36.96 | 82.29 | 12.40 |
| IL-10 | 15.26 | 75.48 | 34.50 | 80.18 | 32.53 | 27.15 | 56.85 |
| IL-12 | 90.00 | 131.25 | 95.00 | 126.25 | 177.50 | 82.50 | 125.00 |

Example 2

Lack of effect of p277(Val$^6$-Val$^{11}$) on Nitric Oxide production in Mouse Macrophages.

Nitric oxide is a proinflammatory mediator produced by macrophages. The classic stimulus for nitric oxide production is lipopolysaccharide (LPS). Other molecules derived from pathogens such as hsp60 also induce macrophages to produce nitric oxide. Nitric oxide is usually produced by cells in conjunction with TNFα, IL-1 and IL-6.

Figure 2:
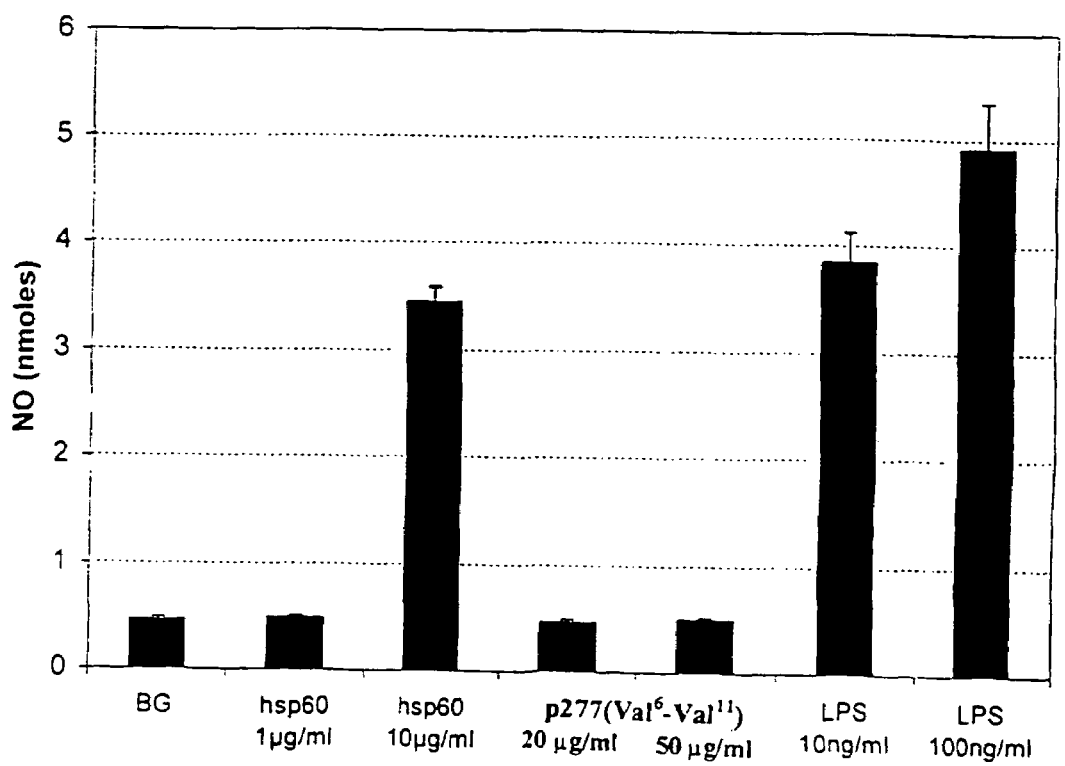
FIG. 2 depicts the lack of effect of p277(Val$^6$-Val$^{11}$) on Nitric Oxide production in mouse macrophages.

The effect of p277(Val$^6$-Val$^{11}$) was tested on the production of nitric oxide from a macrophage cell line both the direct effect and the effect of p277(Val$^6$-Val$^{11}$) on the nitric oxide produced in response to hsp60. Under no conditions did the peptide stimulate nitric oxide production by the cells. Neither did it inhibit the hsp60 induced nitric oxide produced. The effect of p277(Val$^6$-Val$^{11}$) are described in FIG. 2.

The assay method is described in full in WO 01/43691. Briefly, J774 cells (2×10$^5$ cells/assay) were incubated for 48 hours with LPS, hsp60 or p277(Val$^6$-Val$^{11}$) or in inhibition assay, the cells were incubated with hsp60 at various concentrations in the presence or absence of 20 μg/ml p277(Val$^6$-Val$^{11}$). After 48 hours the supernatant was collected and tested for nitric oxide. The test for nitric oxide is performed by mixing an equal volume of the cell supernatant with Griess reagent and measuring the resultant color at 550 nm.

Example 3

Effects of hsp60 Peptides and Analogs on Peripheral Blood Derived Dendritic Cells The assay was based on the protocol described by Re, F. and Strominger, J. L. 2001. Toll-like receptor 2 (Tlr2) and Tlr4 differentially activate human dendritic cells. (J. Biol Chem 276: 37692-9).

Peripheral blood mononuclear cells were prepared from leucocytes from blood lots obtained from the blood bank. The cells were plated at 10$^8$ cells/10 ml/Petri dish in RPMI medium including 10% FCS and allowed to adhere at 37° C. for 2 hours. At the end of this time, the non-adherent cells were washed off the plates with PBS and the adherent cells resuspended in fresh medium as before. The cells were then cultured for at least 8 days with the addition of GM-CSF and IL4 with the medium changed every 4 days. After this time, the cells were harvested and cultured overnight with LPS, zymosan or p277(Val$^6$-Va$^{11}$). The next day, the supernatant was collected for assay of the secreted cytokines (IP-10 and IL-8) and the cells were harvested for investigation of the cell surface antigens (CD83, CD86). CD83 is an antigen characteristic of dendritic cells. Only 30% of the cells in the unfractionated cultures stained positive for this marker which indicates that the culture was not fully differentiated. The second marker, CD86 (B7.2) is characteristic of mature dendritic cells. The marker CD86 is an essential component of the immunological synapse formed between T cells and APC. This synapse consists of CD80 and CD86 on the side of the APC and CD28 and CD40 on the side of the T cell. This is of course in addition to the specific recognition between the T cell receptor and peptide held in the MHC of the APC. T cell recognition of peptide on APC without the concurrent expression of CD86 gives rise to anergy instead of a T cell response.

Figure 3:
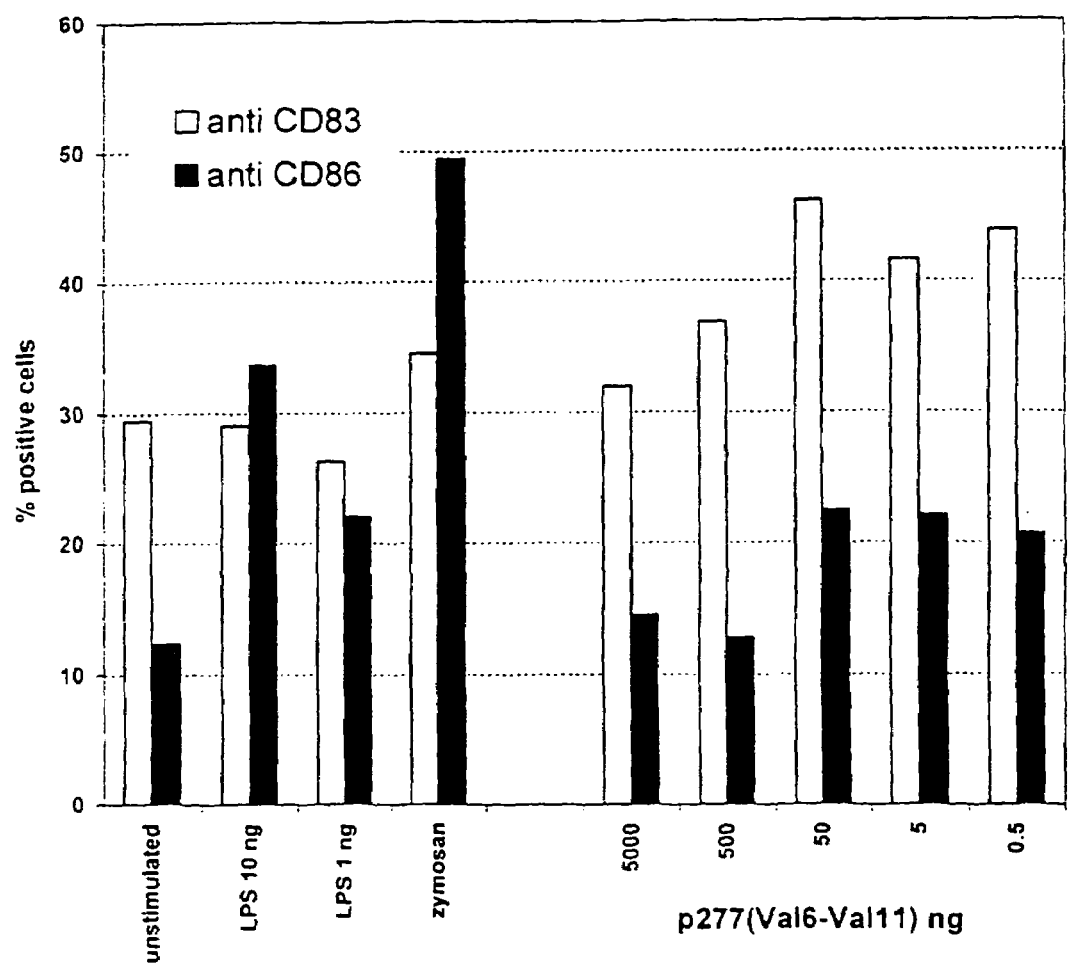
FIG. 3 shows the effect of LPS, zymosan or p277(Val$^6$-Val$^{11}$) on maturation of peripheral blood mononuclear derived dendritic cells, demonstrated by expression of CD83 and CD86.

The results shown in FIG. 3 indicate that there is an increase of maturation after stimulation with LPS, zymosan or p277(Val$^6$-Val$^{11}$) indicated by the increase in the percentage of cells stained with anti-CD86. Out of the cytokines secreted, p277(Val$^6$-Val$^{11}$) stimulation resulted in IL-8 secretion but no IP-10 secretion (table 2). This could suggest that p277(Val$^6$-Val$^{11}$) behaves like zymosan by stimulation through the Toll 2 receptor. This is further tested with antibodies specific to the Toll receptors.

TABLE 2

Influence of stimulation of peripheral blood mononuclear cells with p277(Val$^6$-Val$^{11}$) on IP-10 and IL-8 secretion.

| Stimulus | IP-10 pg/ml | SEM | IL-8 pg/ml | SEM |
|---|---|---|---|---|
| none | −18 | 3.18 | 479 | 23 |
| LPS 10 ng/ml | 2520 | 19.09 | 3131 | 242 |
| zymosan 50 µg/ml | 141 | 20.45 | 2838 | 125 |
| hsp60 1 µg/ml | 31 | 0.91 | | |
| hsp60 0.1 µg/ml | 1 | 10.91 | | |
| hsp60 10 ng/ml | 6 | 12.27 | | |
| p277(Val$^6$-Val$^{11}$) 0.5 µg/ml | 21 | 7.27 | | |
| p277(Val$^6$-Val$^{11}$) 50 ng/ml | 39 | 17.27 | 2574 | 55 |
| p277(Val$^6$-Val$^{11}$) 5 ng/ml | 2 | 5.45 | | |
| p277(Val$^6$-Val$^{11}$) 0.5 ng/ml | −1 | 4.55 | 2368 | 45 |

TABLE 3

Effect of preincubation of THP-1 cells with p277(Val$^6$-Val$^{11}$) and then stimulation with LPS, on IP-10 secretion.

| p277(Val$^6$-Val$^{11}$) ng/ml | % stimulation of IP-10 secretion | SEM |
|---|---|---|
| Background | −92 | 12 |
| 1000 | 45 | 15 |
| 200 | 45 | 9 |
| 40 | 141 | 3 |
| 8 | 77 | 1 |
| 1.6 | 46 | 20 |
| 0.32 | 61 | 4 |
| 0.064 | 52 | 6 |
| 0.0128 | −48 | 0 |

Example 4

Effect on Peripheral Blood Monocytes

Peripheral blood mononuclear cells were prepared from leucocytes of blood lots obtained from the blood bank. The cells were plated at a concentration of 4×10$^6$ cell/ml/well in 24 well tissue culture dishes in medium containing 10% fetal calf serum. The cells were allowed to adhere for 2 hours at 37° C. After this time, non-adherent cells were washed away and the adherent cells incubated in fresh medium containing 10% human AB serum for 6-8 days, changing the medium after 4 days. These culture conditions were reported to give rise to monocytes.

For stimulation the medium was replaced with medium without serum. For preincubation, the cells were exposed overnight to the tested compounds at various concentrations and then LPS was added. The supernatant was collected after a further overnight incubation and tested for various cytokines by ELISA assays.

Figure 4:
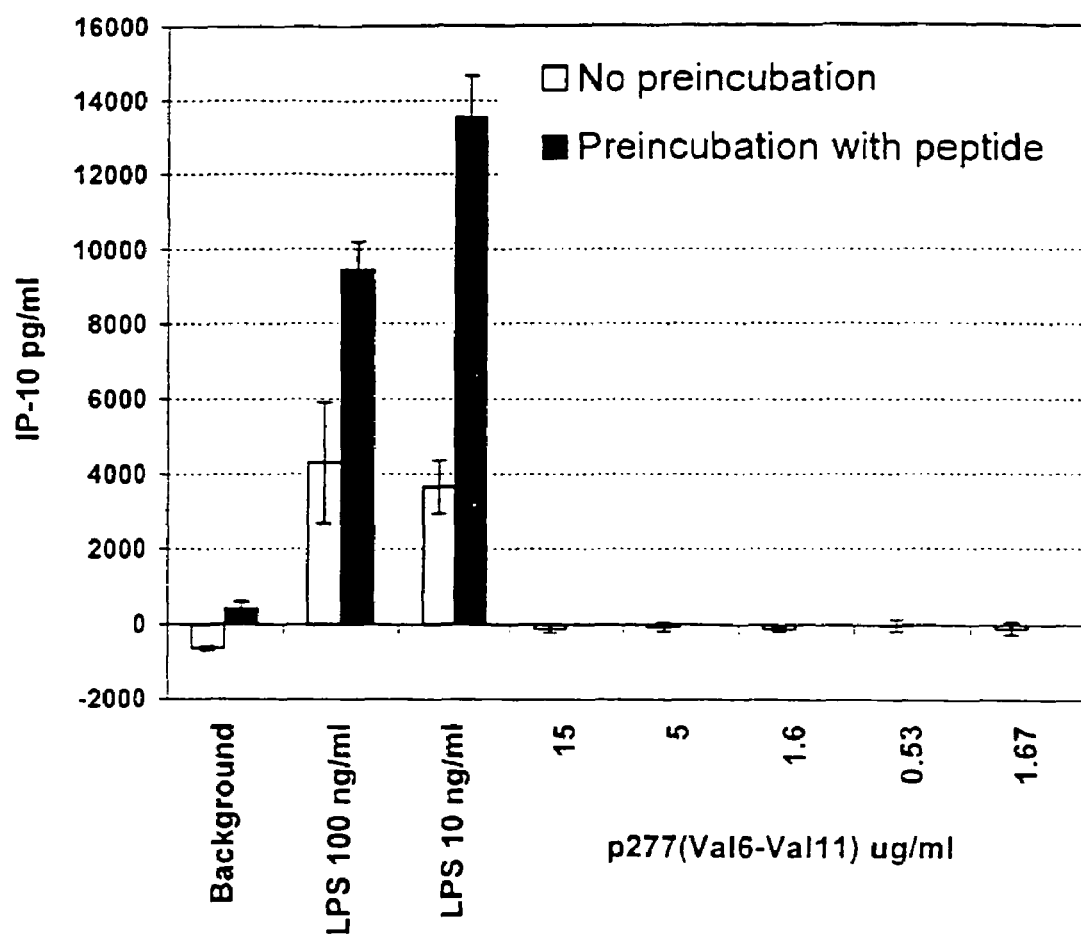
FIG. 4 presents the influence of direct stimulation or pre-incubation of peripheral blood mononuclear cells with p277 (Val$^6$-Val$^{11}$) on IP-10 secretion, after stimulation with LPS.

The results shown in FIG. 4 indicate that direct stimulation with p277(Val$^6$-Val$^{11}$) did not give rise directly to Il-10 but preincubation with this compound did increase the amount of IP-10 produced in response to stimulus with LPS. The cells were also stimulated with hsp60 but this did not give rise to IP-10 either alone or after preincubation with p277(Val$^6$-Val$^{11}$).

Example 5

Effect on Human Cell Lines

The human cell line THP-1 was used for this assay. These cells are pre-monocyte like derived from acute monocytic leukemia and can be differentiated to monocytes by treatment with 100 nM phorbol ester (12-O-tetradecanoylphorbol-13-acetate, PMA) for 72 hours. During this time the cells change morphology from round cells growing in suspension to larger, flat, adherent cells. The sensitivity to stimulus with LPS and hsp60 increases by more than 100 fold with respect to TNF secretion.

Differentiated THP-1 cells incubated with p277(Val$^6$-Val$^{11}$) did not secrete TNF, or IP-10 directly. However, pre-incubation with p277(Val 6-Val$^{11}$) and subsequent stimulus with 10 ng/ml LPS gave rise to an increased amount of IP-10 secreted as shown in table 3. The amount of TNF was not significantly affected.

Example 6

Additional Fragments and Analogs of p277

A number of peptides which are fragments and analogs of p277(Val$^6$-Val$^{11}$), including peptides previously described as critical epitopes of this compound, were tested for Nitric Oxide production in mouse macrophages.

TABLE 4

Fragments and analogs of p277

| Peptide | Sequence | Seq ID No. |
|---|---|---|
| p277 | VLGGGCALLRCIPALDSLTPANED | 2 |
| p277(Val$^6$-Val$^{11}$) DiaPep277 ™ | VLGGGVALLRVIPALDSLTPANED | 3 |
| T-cell epitope | ALLRVIPALDSL | 4 |
| MHC anchors | ALLRVIPALDSL | 5 |
| p277(437-450, Ser$^6$Ser$^{11}$) | VLGGGSALLRSIPA | 6 |
| p277(442-450, Ser$^6$Ser$^{11}$) | SALLRSIPA | 7 |
| p277(442-450, Val$^6$Val$^{11}$) | VALLRVIPA | 8 |

Figure 5:
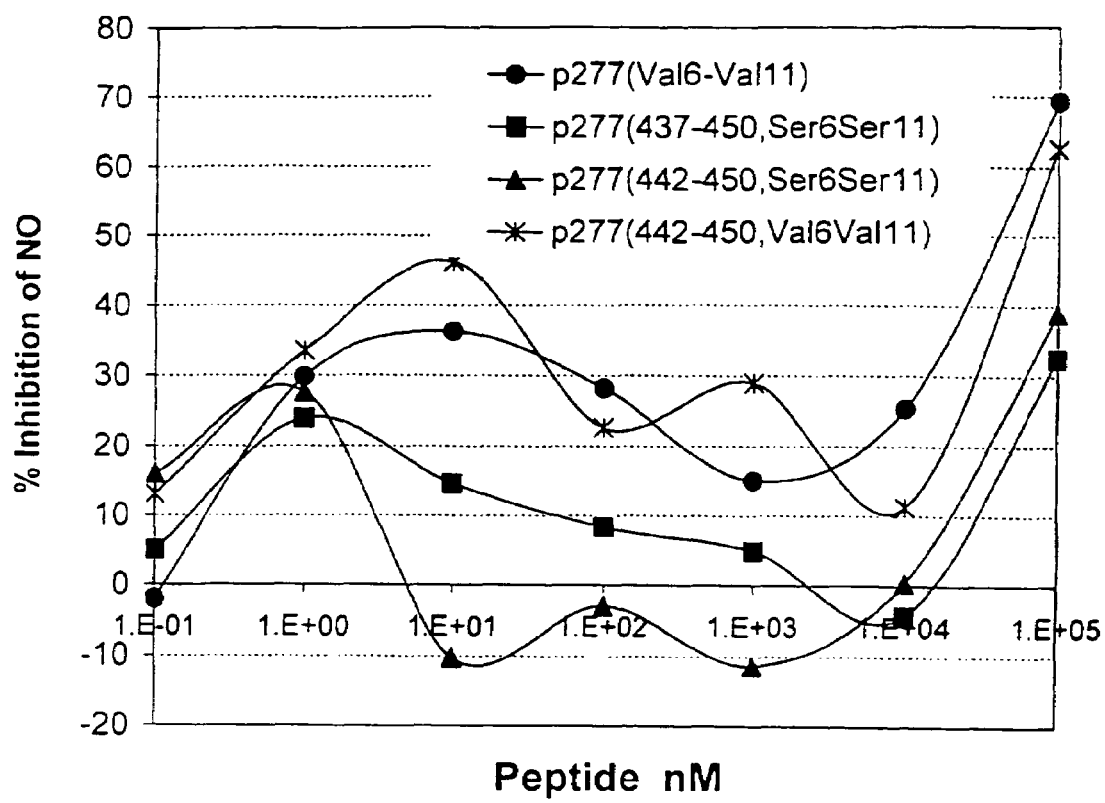
FIG. 5 demonstrates the effects of p277(Val$^6$-Val$^{11}$) and several fragments and analogs thereof, on the secretion of oxygen free radicals from a mouse monocyte cell line.

Although the peptide p277(Val$^6$-Val$^{11}$) was shown to be ineffective both for direct stimulation of TNFα from cell lines test and for inhibition of TNFα secreted as a result of stimulation by LPS or hsp60, the peptide did inhibit the secretion of oxygen free radicals from a mouse monocyte line J774. From tested compounds, only the p277(Val$^6$-Val$^{11}$) and p277(442-450, Val$^6$Val$^{11}$) were effective at inhibition of the oxidative burst as shown in FIG. 5.

Example 7

Additional hsp60 Fragments

The following hsp60 fragments and peptide analogs are tested for influencing Th1-Th2 response of T-cells exposed to educated dendritic cells.

Val-Leu-Gly-Gly-Gly-Ser-Ala-Leu-Leu-Arg-Ser-Ile-Pro-Ala (Seq ID No. 6) disclosed in WO 96/11948.

Gly-Gly-Val-Thr-Leu-Leu-Gln-Ala-Ala-Pro-Ala-Leu-Asp (Seq ID No. 9) disclosed in U.S. Pat. No. 5,958,416.

Any of the hsp60 peptides, derivatives and analogs disclosed in U.S. Pat. Nos. 6,180,103 and 6,110,746.

Example 8

Overlapping Peptides of p277(Val$^6$-Val$^{11}$)

In order to test which epitopes or fragments of the p277 (Val$^6$-Val$^{11}$) are important for activity, additional peptides were prepared using the multiple parallel synthesis method described in detail in example 9. The peptides were designed to include a peptide scan of p277(Val$^6$-Val$^{11}$) starting 2 amino acids before the p277(Val$^6$-Val$^{11}$) (position 435 of hsp60) and proceeding along the sequence synthesizing peptides of 7 to 14 amino acids. These peptides are further tested in the above-mentioned assay systems to define active fragments.

Example 9

Method for Synthesis of Peptide Fragments and Analogs

General Method for Synthesis, Purification and Characterization of Libraries in Multiple Parallel Synthesis (MPS) Format:

The MPS procedure is used as the routine peptide development procedure. Individual peptides, or groups of a few peptides, are synthesized in 96-wells microtiter plates equipped with filters that allow passage of solvent but not of solid phase matrix. A simple and efficient valve apparatus that enable simultaneous closing and opening of all the valves (produced by Millipore) is used. The system utilizes an approach in which each well is equipped with a solvent permeable membrane at the bottom that does not pass particles above a certain size. The process allows to place resin in the wells, perform reaction in solvent, and remove the solvent from all the wells simultaneously by applying vacuum. These special plates, which are available in the standard 96 well format, allow the parallel synthesis of 96 peptides simultaneously. The synthesis scale of the procedure is in the range of 1-5 μmole per well. Following purification by C18 reverse phase columns (SepPak purification), which is also carried in the standard 96 well format, the peptides are routinely dissolved in 1 ml of water to yield a theoretical crude concentration of 1-5 mM (depending of synthesis scale). Monitoring of chemical quality of the resulting peptides is performed by ESI-MS analysis. Analysis of several plates prepared on different occasions by different operators indicated a general success rate of about 80% as judged by the presence of the desired peptide mass in the crude preparation. Further analysis of a peptides from MPS is carried out by LC-MS. The analysis revealed crude peptide quality similar to crud preparations of peptides synthesized individually in large scale. Different steps or the complete process is now performed automatically using automatic peptide synthesizers. According to the present exemplifications, the peptides are currently synthesized automatically using the ACT 396 of Advanced ChemTech, and the heating device Lab Tech 4 of Advanced ChemTech.

Detailed Procedure for Automated Synthesis in MPS Format:

The synthesis was performed on ACT 396 of Advanced ChemTech.

For capacity of 6 μmole 10 mg resin with a substitution of 0.6 mmol/gr is used.

Fmoc deprotection: To each well 500 μl of 25% piperidine in NMP are added twice. The reaction shacked for 15 min. The NMP is removed by suction.

Washing after Fmoc deprotection: the resin is washed by placing 600 μl NMP into each well followed by evacuation of the solution by steam of nitrogen. The washing process is repeated 4 times.

Coupling using HBTU:

Well capacity: 6 μmol; Amount of amino acid per coupling per well: 30 μmol; Amino acid in NMP concentration: 0.2 M; Amino acid volume used: 150 μl; HBTU amount: 30 μmol HBTU concentration: 0.2 M; HBTU volume used: 150 μl; DIEA added: 150 μl of 0.4 M in NMP; Total reaction volume: 450 μl.

The amino acids are dissolved in a solution of HOBT in NMP. The resin is washed by placing 600 μl NMP into each well followed by evacuation of the solution by steam of nitrogen. The washing process is repeated 4 times. The coupling reaction is repeated twice for 1 hour.

Cleavage of the Peptide from the Resin and SepPak Purification: After final Fmoc deprotection the resin is transferred into a deep well microtiter plate, to each well 300 μl of TFA solution containing 2.5% TIS, 2.5% H$_2$O, 2.5% EDT are added. Removal of the TFA is performed by lyophilization. After cleavage the peptides are purified by SepPak.

Manual Synthesis of Peptides and Peptide Analogs

Peptides and peptide analogs were synthesized manually, on 2-chlorotrityl chloride resin. First coupling was performed using 0.7 mmol of Fmoc-AA-OH and 2.8 mmol DIEA. After 1 h the resin was washed with MeOH followed by CH$_2$Cl$_2$ and DMF. The rest of the couplings were performed as the regular Fmoc-chemistry using DIC/HOBt as a coupling reagent, reaction time 1-2 h. At the end of the assembly the resin was washed with CH$_2$Cl$_2$ and dried under reduced pressure. Cleavage of the peptide from the resin was done by a solution of TFA containing 2.5% TIS+2.5% H$_2$O. The crude peptide was purified on C18 reverse phase column.

Example 10

Animal Models for Crohn's Disease

Inflammatory bowel disease (IBD) encompasses 2 distinct chronic, idiopathic, inflammatory disorders that affect the gastrointestinal tract: Crohn's disease and ulcerative colitis. Although these two entities are frequently grouped together, with respect to underlying mechanism of pathology they are different. Crohn's disease predominantly targets the ileum or the colon but can affect any part of the digestive tract, from the mouth to the anus. The deep inflammation of the gastrointestinal tract can cause painful abdominal cramping, fever, rectal bleeding and frequent diarrhea, especially following a meal. In the affected areas there is an inflammatory response with secretion of Th1 type cytokines such as interferon gamma and IL-12.

Based on the current understanding of the pathogenesis of the disease, therapies have been focused on attenuation of the enteric inflammation. The four prominent groups of drugs used to treat Crohn's disease are aminosalicylates, corticosteroids, immuno-modulators and antibiotics. Immunomodulators are aimed to decrease the chronic tissue inflammation seen in Crohn's either by reducing the number of immune cells or by interfering with the pro-inflammatory Th1 type cytokines they produce. The main problem with immunosuppresion is that the body is exposed to the dangers of infection. Imuran (azathioprine) and Purinethol (6-mercaptopurine (6-MP)) are frequently used and may be used in conjunction with corticosteroids. The first treatment approved specifically for Crohn's disease is remicade (infliximab) which is an anti-TNFα antibody. Other treatments in trial are GM-CSF, growth hormone and antibody to ICAM-1 (alicaforsen).

In mouse models of Crohn's disease, antibodies to TNFα, macrophage migration inhibitory factor, and IL-12 have been shown to be effective as well as treatment with TGF-β. All of these indications tend to confirm that Crohn's disease is Th1 mediated and can be ameliorated by modulation of the Th1 response. This makes it suitable for immunomodulation with the compounds of the present invention.

Mouse Models for Crohn's Disease

The dextran sodium sulfate induced colitis mouse model (Ohkawara, et al. 2002, Gastroenterology 123: 256-70, Mahler, et al. 1999, Genomics 55: 147-56), which does not require intervention with cytokines to initiate it or use of specialized strains of mice is used for testing the compounds and compositions according t the present invention. HSP peptides and analogs are injected intraperitoneally 2, 4, and 6 days after addition of dextran sulfate 4% in the drinking water of the mice. The mice are followed for the presence of diarrhea and loss of weight and on day 7, the mice are sacrificed. The intestine is removed and assessed histologically for pathology. As a positive control, the mice are injected with dexamethasone.

While the present invention has been particularly described, persons skilled in the art will appreciate that many variations and modifications can be made. Therefore, the invention is not to be construed as restricted to the particularly described embodiments, rather the scope, spirit and concept of the invention will be more readily understood by reference to the claims which follow.

What is claimed is:

1. A peptide analog of a heat shock protein (Hsp) capable of acting directly on antigen presenting cells for activating other cell types of the immune system, wherein the peptide analog is SEQ ID NO: 8.

2. A pharmaceutical composition comprising the peptide analog of claim 1 and a pharmaceutically acceptable carrier.

3. The pharmaceutical composition of claim 2, further comprising antigen presenting cells.

4. A pharmaceutical composition comprising:
   antigen presenting cells exposed, in the absence of an antigen, to a peptide analog derived from a heat shock protein 60 (Hsp60), wherein the peptide analog is SEQ ID NO: 8, the cells being able to further stimulate T helper cells, and
   a pharmaceutically acceptable carrier.

5. The composition of claim 4, wherein the antigen presenting cells are dendritic cells.

6. The composition of claim 5, wherein the dendritic cells are autologous dendritic cells.

7. The composition of claim 4 consisting essentially of the antigen presenting cells and the peptide analog SEQ ID NO: 8.

* * * * *

UNITED STATES PATENT AND TRADEMARK OFFICE
CERTIFICATE OF CORRECTION

| | | |
|---|---|---|
| PATENT NO. | : 7,576,177 B2 | Page 1 of 1 |
| APPLICATION NO. | : 10/902923 | |
| DATED | : August 18, 2009 | |
| INVENTOR(S) | : Karmon et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 861 days.

Signed and Sealed this
Fifth Day of April, 2016

Michelle K. Lee
*Director of the United States Patent and Trademark Office*